United States Patent [19]

Fushimi et al.

[11] Patent Number: 5,659,097
[45] Date of Patent: Aug. 19, 1997

[54] PROCESS FOR PRODUCING A MONOALKENYL AROMATIC HYDROCARBON COMPOUND

[75] Inventors: Norio Fushimi; Makoto Takagawa, both of Tsukuba, Japan

[73] Assignee: Mitsubishi Gas Chemical Company, Inc., Tokyo, Japan

[21] Appl. No.: 371,301

[22] Filed: Jan. 11, 1995

[30] Foreign Application Priority Data

Jan. 20, 1994 [JP] Japan ............................... 6-004748
Feb. 7, 1994 [JP] Japan ............................... 6-013462

[51] Int. Cl.$^6$ .................................. C07C 15/46; C07C 5/09
[52] U.S. Cl. .......................... 585/438; 585/435; 585/436; 585/452; 585/453; 585/467
[58] Field of Search ............................ 585/435, 438, 585/452, 453, 467, 436

[56] References Cited

U.S. PATENT DOCUMENTS

| | | | |
|---|---|---|---|
| 5,334,794 | 8/1994 | Fushimi et al. | 585/452 |
| 5,344,806 | 9/1994 | Fushimi et al. | 585/452 |
| 5,367,098 | 11/1994 | Fushimi et al. | 585/452 |
| 5,436,381 | 7/1995 | Takagawa et al. | 585/452 |
| 5,444,172 | 8/1995 | Takagawa et al. | 585/452 |
| 5,527,977 | 6/1996 | Takagawa et al. | 585/452 |

FOREIGN PATENT DOCUMENTS

| | | |
|---|---|---|
| 0 547 336 | 6/1993 | European Pat. Off. . |
| 0 569 742 | 11/1993 | European Pat. Off. . |
| WO93/05001 | 3/1993 | WIPO . |

*Primary Examiner*—Glenn A. Caldarola
*Assistant Examiner*—Elizabeth D. Wood
*Attorney, Agent, or Firm*—Frishauf, Holtz, Goodman, Langer & Chick, P.C.

[57] ABSTRACT

A process for producing a monoalkenyl aromatic hydrocarbon which comprises alkenylating a side chain of an aromatic hydrocarbon compound having at least one hydrogen atom at the α-position of a side chain (such as o-xylene) with a conjugated diene having 4 or 5 carbon atoms in the presence of a catalyst slurry prepared by adding an aromatic hydrocarbon compound to a catalyst comprising a alkali metal and an alkali metal compound. In the aforementioned process, it is particularly effective that the catalyst slurry is prepared by adding the aromatic hydrocarbon compound after the aromatic hydrocarbon compound has been deoxygenated and dehydrated by distillation, and the catalyst slurry thus prepared is supplied to the reaction system. According to the aforementioned process, an industrially useful monoalkenyl aromatic hydrocarbon compound, such as a monoalkenylbenzene, can be produced at a high selectivity, in a high yield, and with enhanced safety and stability for a long time.

20 Claims, No Drawings

PROCESS FOR PRODUCING A MONOALKENYL AROMATIC HYDROCARBON COMPOUND

BACKGROUND OF THE INVENTION

1. Field of the Invention

The present invention relates to a process for producing a monoalkenyl aromatic hydrocarbon compound. More particularly, the present invention relates to a process for producing a monoalkenyl aromatic hydrocarbon compound by alkenylating a side chain of an aromatic hydrocarbon compound by using a conjugated diene having 4 or 5 carbon atoms.

Monoalkenyl aromatic hydrocarbon compounds, such as monoalkenylbenzenes, are useful as intermediate materials for various organic compounds, such as monomers of macromolecular compounds, drugs, and the like. For example, 5-(o-tolyl)-2-pentene produced from o-xylene and 1,3-butadiene can be converted into industrially useful 2,6-naphthalenedicarboxylic acid by the successive ring closure, dehydrogenation, isomerization, and oxidation.

2. Description of the Related Arts

For producing a monoalkenylbenzene by alkenylating a side chain of an aromatic hydrocarbon compound with a conjugated diene having 4 or 5 carbon atoms, a process using an alkali metal, such as sodium and potassium, or an alloy thereof, as the catalyst has been known.

For example, a process using sodium metal as the catalyst is described in German Patent No. 557514. A process using potassium metal as the catalyst is described in Japanese Patent Publication No. Showa 50(1975)-17973. Processes using a potassium/sodium alloy or a mixture of potassium and sodium metals are described in Japanese Patent Publication Nos. Showa 50(1975)-17975 and Showa 51(1976)-8930.

A process using a product obtained by heat treatment of an alkali meal and an alkali metal compound as the catalyst is also known. For example, processes using a mixture obtained by heat treatment of a potassium compound and sodium metal as the catalyst are described in Japanese Patent Application Laid-Open Nos. Showa 47(1972)-27929 and Showa 47(1972)-31935.

It has been discovered by the group including the present inventors that a product obtained by heat treatment of a supported potassium compound and sodium metal shows the activity in the side chain alkenylation (specifications of United States Patent No. 5,344,806, and European Patent No. 569742A).

Among the processes described above, wherein when sodium metal is solely used as the catalyst without any treatment does not show either sufficient activity or sufficient selectivity and cannot be practical for the industrial process. Potassium metal, a potassium/sodium alloy, or a mixture of potassium and sodium metals as the catalyst shows a high catalytic activity. However, the catalysts react violently with oxygen and water. Therefore, when the process is industrially conducted, the possibility of hazard such as fire and explosion is large and the process has many problems with respect to safety.

The process using a mixture obtained by heat treatment of an alkali metal and an alkali metal compound at a high temperature is characterized in that neither potassium metal nor a potassium alloy is used for the reaction. However, when the powder catalyst prepared is transferred to a reactor or the like, operation problems, such as choking of the apparatus, tend to arise. Because the powder catalyst is a very reactive material, the operation having these problems is not preferable for the industrial embodiment from the standpoint of safety.

To overcome the problems described above, processes in which the catalyst is not transferred but the catalyst preparation and the production of an alkenylbenzene are conducted in the same reactor have been proposed in Japanese Patent Application Laid-Open Nos. Showa 47(1972)-27929 and Showa 47(1972)-31935. However, these processes show low process efficiencies in the industrial application and are not always practical.

When a small amount of water or oxygen is contained in the raw material, the catalyst is deactivated by the reaction with water or oxygen even when the amount of water or oxygen does not cause problems on the safety. Therefore, a large amount of the catalyst must be used to obtain a monoalkenylbenzene in a high yield.

SUMMARY OF THE INVENTION

It was discovered by the present inventors that, for producing a monoalkenyl aromatic hydrocarbon compound by alkenylating the α-position of a side chain of an aromatic hydrocarbon compound by using a conjugated diene having 4 or 5 carbon atoms, the monoalkenyl aromatic hydrocarbon compound can be produced safely and efficiently, with a low cost, and in a high yield, when a catalyst prepared from an alkali metal and an alkali metal compound is formed into a slurry with the aromatic hydrocarbon compound used as the raw material, and then the slurry containing the catalyst thus prepared is supplied to the reaction system. Furthermore, it was discovered that the monoalkenyl aromatic hydrocarbon compound can be produced more efficiently and more safely by deoxygenating and dehydrating the aromatic hydrocarbon compound used as the raw material by distillation in advance, according to necessity. The present invention has been completed on the basis of the discoveries.

An object of the present invention is to provide a process for producing a monoalkenyl aromatic hydrocarbon compound with a high yield and a low cost by a safer process.

Another object of the present invention is to provide a process for producing a monoalkenyl aromatic hydrocarbon compound efficiently with enhanced stability for a long time while activity of the catalyst is kept at a high level.

The present invention provides a process for producing a monoalkenyl aromatic hydrocarbon compound which comprises alkenylating a side chain of an aromatic hydrocarbon compound having at least one hydrogen atom at the α-position of a side chain with a conjugated diene having 4 or 5 carbon atoms in the presence of a catalyst slurry prepared by adding an aromatic hydrocarbon compound to a catalyst comprising an alkali metal and an alkali metal compound.

In the process of the present invention, a monoalkenyl aromatic hydrocarbon compound can be produced more efficiently by deoxygenating and dehydrating the aromatic hydrocarbon compound used as the raw material by distillation in advance.

According to the process of the present invention, transfer of the catalyst is facilitated by forming the prepared catalyst into a slurry, and it is not necessary that the same vessel is used both for the preparation of the catalyst and for the reaction of the alkenylation. Therefore, the preparation of the catalyst and the reaction of alkenylation can be conducted in separate vessels. Furthermore, the surface of the catalyst is protected by immersing the catalyst in the aromatic hydrocarbon compound and possibility of hazard, such as fire from the catalyst by the reaction of the catalyst with oxygen, is small even when the catalyst is exposed to the air. Thus, a remarkable effect is exhibited with respect to enhancement of the safety.

Because both the amounts of oxygen and water in the aromatic hydrocarbon compound are small when the aromatic hydrocarbon compound is used as the raw material after it is deoxygenated and dehydrated, the catalyst used for alkenylation of the side chain suffers little damage by the contact of the catalyst with the aromatic hydrocarbon compound. Thus, a remarkable effect is exhibited on decrease in the amount of the catalyst and increase in the life of the catalyst by the treatment of deoxygenating and dehydrating the raw material.

DESCRIPTION OF PREFERRED EMBODIMENTS

As the aromatic hydrocarbon compound having at least one hydrogen atoms bonded to the α-position of a side chain, the following compounds are more specifically used.

Examples of the aromatic hydrocarbon compound used as the raw material include monocyclic aromatic hydrocarbon compounds and polycyclic aromatic hydrocarbon compounds. Examples of the monocyclic aromatic hydrocarbon compound include: monoalkylbenzenes, such as toluene, ethylbenzene, n-propylbenzene, isopropylbenzene, n-butylbenzene, sec-butylbenzene, isobutylbenzene, and the like; dialkylbenzenes, such as o-xylene, m-xylene, p-xylene, o-ethyltoluene, m-ethyltoluene, p-ethyltoluene, o-diethylbenzene, m-diethylbenzene, p-diethylbenzene, and the like; trialkylbenzenes, such as mesitylene, pseudocumene, and the like; and polyalkylbenzenes, such as 1,2,3,5-tetramethylbenzene, 1,2,4,5-tetramethylbenzene, pentamethylbenzene, hexamethylbenzene, and the like. Examples of the polycyclic aromatic hydrocarbon compound include: 1-methylnaphthalene, 2-methylnaphthalene, dimethylnaphthalenes, tetrahydronaphthalene, indan, and the like.

As the conjugated diene having 4 or 5 carbon atoms which is used as the other raw material, 1,3-butadiene, 1,3-pentadiene, or isoprene is preferably used.

In the present invention, the catalyst comprising an alkali metal and an alkali metal compound is used. As the alkali metal compound, any type of alkali metal compound can be used. Due to high activity and economic advantage, potassium hydroxide, potassium carbonate, potassium phosphate, potassium aluminate, potassium acetate, potassium methoxide, potassium ethoxide, sodium hydroxide, sodium carbonate, sodium phosphate, sodium aluminate, sodium acetate, sodium methoxide, sodium ethoxide, and the like, are preferably used.

The alkali metal compound used for the catalyst of the present invention can be used in the supported form. The support may be any suitable for the use, such as an oxide of an alkaline earth metal like magnesium oxide, calcium oxide, or the like; a carbon material like graphite, amorphous carbon or the like; alumina; or zirconium oxide.

A compound comprising a mixture of potassium hydroxide and aluminum hydroxide calcined at 500° to 700° C. can be used as the alkali metal compound.

The compounds which comprise potassium hydroxide, potassium carbonate, potassium phosphate, potassium aluminate, potassium acetate, potassium methoxide, potassium ethoxide, sodium hydroxide, sodium carbonate, sodium phosphate, sodium aluminate, sodium acetate, sodium methoxide, sodium ethoxide, or the like, supported on a support such as an oxide of an alkaline earth metal like magnesium oxide, calcium oxide, or the like, a carbon material like graphite, amorphous carbon, or the like, alumina, or zirconium oxide, can be prepared by mixing the components, followed by calcining the mixture at 400° C. or more, preferably 500° to 700° C. The mixture may be dried before the calcination.

For mixing the components, it may be applicable to immerse or to knead an aqueous solution of the alkali metal compound with the support described above.

The alkali metal used in this invention may be lithium, sodium, potassium, rubidium, or cesium. Sodium or potassium is preferably used because of getting a high catalytic activity as well as economic advantage.

Preparation of the catalyst by mixing the alkali metal compound and the alkali metal can be conducted by various methods. For example, the components are mixed by heating to or above the melting point of the alkali metal in an inert gas. The inert gas is may be any of the gases which are substantially not reactive with the prepared catalyst in the condition of the catalyst preparation, such as nitrogen, helium, argon, or the like. When lithium is used as the alkali metal, nitrogen is not preferable because lithium is reactive with nitrogen.

The temperature of the preparation of the catalyst used in the present invention is generally in the range of the melting point of the alkali metal to 500° C., preferably in the range of the melting point of the alkali metal to 300° C. The period of the treatment by heating is generally in the range of 5 to 300 minutes. When the temperature is lower than the melting point of the alkali metal, it is difficult that the alkali metal and the alkali metal compound are effectively mixed with each other to achieve the homogeneous dispersion because the alkali metal does not melt. Therefore, the preparation of the catalyst requires a long time in this condition, and a temperature below the melting point of the alkali metal is not practical. The catalyst may be prepared at a temperature higher than 500° C. However, handling an easily ignited material at a high temperature is not preferable for an industrial process.

The amount of the alkali metal may be suitably selected depending on the condition of the application, and is generally in the range of 0.01 to 10 atom, preferably 0.02 to 5 atom, of the alkali metal per 1 atom of the alkali metal component in the alkali metal compound. When the mount of the alkali metal used is outside of this range, the activity of the catalyst comprising the alkali metal and the alkali metal compound is not sufficiently exhibited and a large amount of the catalyst is occasionally required to obtain the necessary catalytic activity.

The powder catalyst is formed into a slurry with the aromatic hydrocarbon compound used for the reaction and the slurry thus prepared is supplied to the reactor. An aromatic hydrocarbon compound is added to the catalyst prepared to form the catalyst into a slurry and the desired reaction is conducted in the presence of the catalyst in the form of the slurry.

The aromatic hydrocarbon compound used for the preparation of the slurry of the catalyst is the aromatic hydrocarbon compound used for the reaction as the raw material. However, another aromatic hydrocarbon compound of the same type as or a different type from the aromatic hydrocarbon compound used for the reaction as the material may also be used.

The transfer of the powder catalyst is not preferred because of causing many problems in the industrial process.

The powder catalyst may cause choking in the process of the transfer, and tends to be left remaining in the vessel for the catalyst preparation and the pipings for the transfer, and quantitative transfer of the catalyst is difficult.

The amount of the aromatic hydrocarbon compound added to the powder catalyst for the preparation of a slurry is not particularly limited but can be suitably selected in accordance with the condition. The amount is generally 1 to 50 parts by weight, preferably 2 to 40 parts by weight, per 1 part by weight of the catalyst. When the amount of the aromatic hydrocarbon compound is less than the specified range, the slurry tends to lose its fluidity. When the amount is more than the specified range, the vessel with a large capacity may be required for the catalyst preparation. Therefore, an amount outside of the specified range is not preferable for the industrial application.

The catalyst used in the process of the present invention which is prepared from an alkali metal and an alkali metal compound has itself a very high reactivity and causes a hazard such as ignition by the reaction of the catalyst and oxygen when the catalyst is exposed to the air. However, when the catalyst is immersed into an aromatic hydrocarbon compound, the surface of the catalyst is protected with the aromatic hydrocarbon compound and the catalyst does not cause ignition even when the catalyst is exposed to the air. The method of transferring the catalyst in the form of a slurry is very effective not only for improving on the industrial process but also for enhancing the safety.

When a reaction is conducted using the catalyst provided to the reaction system as described above, it is preferable that the raw materials are supplied to the reactor containing the slurry of the catalyst by a batch process or a semi-batch process. As the mode of the reaction, a complete mix flow method in which the catalyst and the raw materials are supplied to the reactor continuously, or a fixed bed flow method in which the raw materials are passed through the reactor packed with the catalyst, can be proposed. The complete mix flow method is not preferable for the industrial process because the selectivity to the monoalkenyl aromatic hydrocarbon compound is low. Many stages of the reactor are required for increasing the selectivity and the cost of the equipment is increased. The fixed bed flow method is also difficult because selectivity to the product is low, and problems such as choking of the reactor tend to arise when a powdery catalyst is used as the fixed bed.

For the embodiment of the present invention, it is effective that the aromatic hydrocarbon compound is deoxygenated and dehydrated by distillation in advance.

As the method of deoxygenating and dehydrating the aromatic hydrocarbon compound, distillation, drying with molecular sieves, bubbling of nitrogen, cryogenic separation, and the like methods, can be proposed. After extensive studies, it has been found that distillation is very effective for the operation of the process. The distillation method shows the following efficiencies: water and oxygen can be eliminated effectively and surely; the deoxygenation and the dehydration can be conducted by a single process, and the raw aromatic hydrocarbon compound can be treated continuously.

The distillation column used for deoxygenating and dehydrating the aromatic hydrocarbon compound does not require any extraordinary facilities or ability. The distillation may be conducted at either an atmospheric pressure, an increased pressure, or a reduced pressure. The operation at an atmospheric pressure or an increased pressure is preferable for avoiding penetration of oxygen and water from the outside. It is also preferable that the distillation system is sealed with dry nitrogen. Any of batch distillation and continuous distillation may be adopted for the distillation. During the distillation, oxygen in the aromatic hydrocarbon compound is discharged from the system through a purge line. It is preferable that water is removed from the refluxing vessel by a suitable method because water is accumulated in the refluxing vessel. It is possible that water and oxygen in the bottom product from the distillation column can be reduced substantially to a level of zero. When the bottom product is used as the raw material of the reaction, the reaction can be conducted in the condition in which the amounts of catalyst poisons, such as water and oxygen, are extremely small. The objective product can be obtained with a high yield by using a small mount of the catalyst and, as the result, a remarkable increase in the life of the catalyst can be accomplished.

The temperature of the reaction in the process of the present invention is generally in the range of 50° to 300° C., preferably 90° to 200° C. When the temperature is lower than the specified range, a sufficient rate of the reaction cannot be obtained and the selectivity tends to be decreased. When the temperature is higher than the specified range, byproducts such as tar are increased. Thus, a temperature outside of the specified range is not preferable.

It is sufficient that the pressure of the reaction is kept at a value for keeping the raw aromatic hydrocarbon compound and the products substantially in the liquid phase. The pressure is generally in the range of 0.05 to 50 atm, preferably 0.1 to 20 arm, as the absolute pressure.

The amount of the conjugated diene having 4 or 5 carbon atoms which is used as the other raw material in combination with the aromatic hydrocarbon compound in the present invention is generally in the range of 0.01 to 1 mol, preferably 0.03 to 0.5 mol, per 1 tool of the aromatic hydrocarbon compound. When the amount is less than the specified range, the condition is not practical. When the amount is more than the specified range, a monoalkenyl aromatic hydrocarbon compound, such as a monoalkenylbezene, formed by the reaction reacts further with the conjugated diene and amounts of by-products in which two or more molecules of the conjugated diene are added to one molecule of the aromatic hydrocarbon are increased. Polymerization of the conjugated diene tends to take place as well. Therefore, an amount of the conjugated diene outside of the specified range is not preferable.

The amount of the catalyst in the present invention, a so-called catalytic amount, is sufficient and is not particularly limited. The amount of the catalyst is generally in the range of 0.01% by weight or more, preferably 0.05% by weight or more, of the raw aromatic hydrocarbon compound used.

The reaction period in the process of the present invention is generally 0.1 to 10 hours.

Separation of the reaction solution and the catalyst after the reaction can be made easily by a conventional method, such as precipitation, centrifugal separation, and filtration. The catalyst separated may be recycled to the reaction system or may be recycled to the process for the catalyst preparation after being treated with appropriate processes, such as removal of attached organic compounds by burning in the air and washing with water.

According to the process of the present invention, an industrially useful monoalkenyl aromatic hydrocarbon compound, such as a monoalkenylbenzenes, can be produced from an aromatic hydrocarbon compound and a conjugated diene in a high yield, at a low cost, and by a process of enhanced safety.

The invention will be understood more readily with reference to the following examples; however, these examples are intended to illustrate the invention and are not to be construed to limit the scope of the invention.

EXAMPLE 1

To a distillation apparatus (a bottom capacity of 2 liters), 1 kg of o-xylene (an oxygen content of 50 ppm and a water content of 140 ppm) was supplied and totally refluxed in a nitrogen atmosphere at an atmospheric pressure at 145° C. for 30 minutes.

At the top of the distillation column, o-xylene was supplied at a rate of 1 liter/hour and a deoxygenation and a dehydration treatment was conducted by the continuous distillation. o-Xylene obtained as the bottom product had a content of oxygen of 0 ppm and a content of water of 3 ppm.

Into a vessel for the catalyst preparation (capacity, 10 liters), 1 kg of a support comprising potassium hydroxide and alumina (containing 2 parts by weight of alumina per 1 part by weight of potassium hydroxide) was supplied, and then 120 g of sodium metal was added under a stirring at 180° C. in a nitrogen atmosphere. The mixture was stirred for 30 minutes at the same temperature. After cooling the vessel for the catalyst preparation to 140° C., 4 kg of o-xylene which had been deoxygenated and dehydrated by the distillation described above was added to the vessel in a nitrogen stream to prepare a slurry. The slurry thus prepared was transferred to a reactor. The whole amount of the slurry could be transferred to the reactor. To the reactor, 96 kg of o-xylene which had been deoxygenated and dehydrated by the distillation described above was added and heated to 140° C. Under a vigorous stirring, 7 kg of 1,3-butadiene was added over the time of 1 hour for the reaction. After the reaction was finished, the stirring was stopped to precipitate the catalyst and the supernatant liquid of the reaction product was taken out.

A part of the reaction solution was taken out as a sample and analyzed by gas chromatography. Yield of the object compound 5-(o-tolyl)-2-pentene was 82.5% based on 1,3-butadiene used.

To the reaction vessel from which the reaction solution had been taken out as described above, 96 kg of o-xylene was newly added and the reaction was conducted similarly. Yield of 5-(o-tolyl)-2-pentene was 81.9

The same operation was repeated 5 times. The yield was kept at 80 % or more and no deactivation was observed.

Comparative Example 1

A catalyst was prepared and transferred to the reactor and the reaction was conducted, by the same method as that in Example 1 except that the amount of o-xylene added for the preparation of the slurry was changed to 0.5 kg.

The mixture of the catalyst and o-xylene obtained had a too high viscosity and a poor fluidity. A half or more of the amount of the mixture was left remaining in the vessel for the catalyst preparation and in the piping for the transfer. Thus, transfer of the whole amount of the mixture was not possible. As the results, yield of 5-(o-tolyl)-2-pentene, which was 80.7% in the first run of the reaction, decreased to 77.4% in the fifth run of the reaction. Thus, the catalyst activity showed the tendency to decrease in the repeated runs of the reaction.

EXAMPLE 2

A catalyst was prepared and transferred to the reactor and the reaction was conducted, by the same method as that in Example 1 except that the prepared slurry was exposed to the air.

Yields of 5-(o-tolyl)-2-pentene were 80% or more in the five repeated runs of the reaction.

Comparative Example 2

The catalyst prepared by the same method as that in Example 1 was exposed to the air without forming into a slurry. Vigorous generation of heat from the catalyst was observed. To this catalyst, 96 kg of o-xylene was added and the reaction was attempted by the same method as that in Example 1. The catalyst activity was entirely lost and the object compound 5-(o-tolyl)-2-pentene was not obtained.

EXAMPLE 3

A catalyst was prepared and transferred to the reactor and the reaction was conducted, by the same method as that in Example 1 except that 1 kg of a support comprising potassium hydroxide and magnesium oxide (containing 2 parts by weight of magnesium oxide per 1 part by weight of potassium hydroxide) was used in place of the support comprising potassium hydroxide and alumina.

Yields of 5-(o-tolyl)-2-pentene were 80% or more in the five repeated runs of the reaction.

EXAMPLE 4

A catalyst was prepared and transferred to the reactor and the reaction was conducted, by the same method as that in Example 1 except that 1 kg of a support comprising potassium hydroxide and zirconium oxide (containing 2 parts by weight of zirconium oxide per 1 part by weight of potassium hydroxide) was used in place of the support comprising potassium hydroxide and alumina.

Yields of 5-(o-tolyl)-2-pentene were 80% or more in the five repeated runs of the reaction.

What is claimed is:

1. A process for producing a monoalkenyl aromatic hydrocarbon which comprises alkenylating a side chain of a first aromatic hydrocarbon compound which is deoxygenated and dehydrated by distillation, said first aromatic hydrocarbon compound having at least one hydrogen atom at the α-position of a side chain, with a conjugated diene having 4 or 5 carbon atoms, in the presence of a catalyst slurry, said catalyst slurry prepared by adding a second aromatic hydrocarbon compound to a catalyst, said catalyst obtained by heating an alkali metal and an alkali metal compound to or above the melting point of the alkali metal, in an inert gas.

2. The process according to claim 1, wherein the first aromatic hydrocarbon compound is the same as the second aromatic hydrocarbon compound.

3. The process according to claim 1, wherein the alkali metal is sodium or potassium.

4. The process according to claim 1, wherein said alkali metal compound is selected from the group consisting of potassium hydroxide, potassium carbonate, potassium phosphate, potassium aluminate, sodium hydroxide, sodium carbonate, sodium phosphate and sodium aluminate; and said alkali metal compound is supported on alumina, an oxide of an alkaline earth metal, zirconium oxide, or a carbon material.

5. The process according to claim 1, wherein the alkali metal compound is obtained by the calcination of a mixture of potassium hydroxide and aluminum hydroxide at 500° to 700° C.

6. The process according to claim 1, wherein the second aromatic hydrocarbon compound is in an amount of 1 part by weight or more to less than 50 parts by weight per 1 part by weight of the catalyst.

7. The process according to claim 1, wherein the first aromatic hydrocarbon compound tetrahydronaphthalene and indan.

8. The process according to claim 1, wherein the conjugated diene having 4 or 5 carbon atoms is selected from the group consisting of 1,3-butadiene, 1,3,-pentadiene, and isoprene.

9. The process according to claim 1, wherein for the deoxygenated and dehydrated first aromatic hydrocarbon compound a concentration of oxygen is decreased to 1 ppm or less and a concentration of water is decreased to 5 ppm or less, respectively, by the distillation.

10. The process according to claim 4, wherein the first aromatic hydrocarbon compound is selected from the group consisting of toluene, ethylbenzene, n-propylbenzene, isopropylbenzene, n-butylbenzene, sec-butylbenzene, isobutylbenzene, o-xylene, m-xylene, p-xylene, o-ethyltoluene, m-ethyltoluene, p-ethyltoluene, o-diethylbenzene, m-diethylbenzene, tetramethylbenzene, 1,2,4,5-tetramethylbenzene, pentamethylbenzene, hexamethylbenzene, 1-methylnaphthalene, 2methylnaphthalene, dimethylnaphthalene, tetrahydronaphthalene and indan.

11. The process according to claim 1, wherein the conjugated diene is selected from the group consisting of 1,3-butadiene, 1,3-pentadiene and isoprene.

12. The process according to claim 11 wherein the alkali metal is selected from the group consisting of lithium, sodium and potassium.

13. The process according to claim 12, wherein the alkali metal is in an amount of 0.01 to 10 atom per 1 atom of the alkali metal compound.

14. The process according to claim 12, wherein the alkali metal is in an amount of 0.02 to 5 atom per 1 atom of the alkali metal compound.

15. The process according to claim 14, wherein the second aromatic hydrocarbon compound is in an amount of 1 to 50 parts by weight per 1 part by weight of the catalyst.

16. The process according to claim 14, wherein the second aromatic hydrocarbon compound is in an amount of 2 to 40 parts by weight per 1 part by weight of the catalyst.

17. The process according to claim 16, wherein the process is carried out at a temperature of 50° to 300° C., at a pressure of 0.05 to 50 atm and for a reaction time of 0.16 to 10 hours.

18. The process according to claim 17, wherein the temperature is 90° to 200° C. and the pressure is 0.1 to 20 atm.

19. The process according to claim 18, wherein the conjugated diene is in an amount of 0.01 to 1 mol per 1 mol of the first aromatic hydrocarbon compound; and the catalyst is in an amount of 0.01% by weight or more of the first aromatic hydrocarbon compound.

20. The process according to claim 18, wherein the conjugaged diene is in an amount of 0.03 to 0.5 mol per 1 mol of the first aromatic hydrocarbon compound; and the catalyst is in an amount of 0.05% by weight or more of the first aromatic hydrocarbon compound.

* * * * *